(12) United States Patent
Kim et al.

(10) Patent No.: US 9,701,774 B2
(45) Date of Patent: Jul. 11, 2017

(54) METALLOCENE COMPOUND AND METHOD OF PREPARING THE SAME

(71) Applicant: LG CHEM, LTD., Seoul (KR)

(72) Inventors: Se Young Kim, Daejeon (KR); Min Seok Cho, Daejeon (KR); Dae Hwan Kim, Daejeon (KR); Sung Min Lee, Daejeon (KR); Sung Ho Park, Daejeon (KR); Ki Soo Lee, Daejeon (KR); Bog Ki Hong, Daejeon (KR); Yong Ho Lee, Daejeon (KR); Kyung Jin Cho, Daejeon (KR); Chang Woan Han, Daejeon (KR); Jin Young Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/911,995

(22) PCT Filed: Jun. 2, 2015

(86) PCT No.: PCT/KR2015/005530
§ 371 (c)(1),
(2) Date: Feb. 12, 2016

(87) PCT Pub. No.: WO2015/186952
PCT Pub. Date: Dec. 10, 2015

(65) Prior Publication Data
US 2016/0194422 A1    Jul. 7, 2016

(30) Foreign Application Priority Data
Jun. 3, 2014    (KR) .................. 10-2014-0067698

(51) Int. Cl.
| | | |
|---|---|---|
| *C07F 17/00* | (2006.01) | |
| *C08F 4/6592* | (2006.01) | |
| *C08F 10/00* | (2006.01) | |
| *C08F 210/16* | (2006.01) | |
| *C08F 4/659* | (2006.01) | |

(52) U.S. Cl.
CPC ............ *C08F 210/16* (2013.01); *C07F 17/00* (2013.01); *C08F 4/6592* (2013.01); *C08F 4/65908* (2013.01); *C08F 4/65912* (2013.01); *C08F 4/65925* (2013.01); *C08F 10/00* (2013.01)

(58) Field of Classification Search
CPC  C07F 17/00; C08F 4/65925; C08F 4/659108; C08F 6/65912; C08F 10/00; C08F 4/65908
See application file for complete search history.

(56) References Cited

U.S. PATENT DOCUMENTS

| | | | |
|---|---|---|---|
| 6,566,544 B1 | 5/2003 | Waymouth et al. | |
| 6,894,131 B2 | 5/2005 | McCullough et al. | |
| 2001/0031834 A1* | 10/2001 | Ushioda | ................. C08L 23/12 525/240 |
| 2002/0002261 A1* | 1/2002 | Yahata | .................... C08F 10/00 526/351 |

FOREIGN PATENT DOCUMENTS

| | | |
|---|---|---|
| JP | 2013-122013 A | 6/2013 |
| KR | 10-2008-0057279 A | 6/2008 |
| KR | 10-2008-0104331 A | 12/2008 |
| KR | 10-2012-0075937 A | 7/2012 |
| KR | 10-2014-0049452 A | 4/2014 |
| WO | 2008/084931 A1 | 7/2008 |

* cited by examiner

*Primary Examiner* — Caixia Lu
(74) *Attorney, Agent, or Firm* — Dentons US LLP

(57) ABSTRACT

Provided are a metallocene compound having a novel structure capable of preparing a polyolefin having a broad molecular weight distribution and a high molecular weight, and a method of preparing the same. The metallocene compound according to the present invention includes a non-crosslinked catalyst structure, and implements copolymerizability in an ansa-type catalyst level, thereby preparing a polyolefin having a high molecular weight of 300,000 or more.

9 Claims, No Drawings

METALLOCENE COMPOUND AND METHOD OF PREPARING THE SAME

CROSS-REFERENCE TO RELATED APPLICATION

This application is a National Stage Entry of International Application No. PCT/KR2015/005530, filed Jun. 2, 2015, and claims the benefit of and priority to Korean Application No. 10-2014-0067698, filed on Jun. 3, 2014, all of which are hereby incorporated by reference in their entirety for all purposes as if fully set forth herein.

BACKGROUND OF THE INVENTION (a) Field of the Invention

The present invention relates to a non-crosslinked metallocene catalyst having a novel structure for preparing polyethylene having high polymerizability, and a method of preparing the same.

(b) Description of the Related Art

A Ziegler-Natta catalyst which is widely applied in a conventional commercial process is a multi-site catalyst, and thus, since it is characterized in that a produced polymer has a broad molecular weight distribution, and the composition distribution of the comonomer is non-uniform, there is a limitation in securing desired physical properties.

However, a metallocene catalyst is a single-site catalyst having one kind of active point, and thus it has advantages in that the produced polymer has a narrow molecular weight distribution, and molecular weight, tacticity, crystallinity, in particular reactivity of a comonomer, may be significantly adjusted depending on the structures of a catalyst and a ligand.

As the metallocene catalyst, International Laid-Open Patent Publication No. 2008/084931 discloses a transition metal compound coordinated with a monocyclopentadienyl ligand to which an amido group is introduced. However, since a polyolefin polymerized by the metallocene catalyst according to the method has a narrow molecular weight distribution, when applied to some products there is a difficulty in field application, for example, productivity is significantly decreased due to an extrusion load and the like. Thus, in this regard, many efforts have been made to control the molecular weight distribution of a polyolefin. A polymer having a narrow molecular weight distribution has low melt flowability, low melt tension, and poor moldability, and may act as a factor for decreasing stiffness.

However, a metallocene catalyst precursor generally used in the preparation of a low molecular weight polyethylene has a small-sized ligand coordinated to a central metal, and has a structure in a non-crosslinked form. Though these catalysts may produce a low molecular weight polymer with high activity, they have a problem in that copolymerizability of a comonomer such as 1-hexene is relatively reduced by a small bite angle (Cp-Metal-Cp) as compared with other ansa-type catalysts.

In addition, in the case that a substituent is further introduced to the ligand, or bulk is increased, in order to implement a medium-low molecular weight based on supported polymerization, a molecular weight increase effect may be obtained, but it is a general trend to result in further decreased copolymerizability.

Therefore, there is need for development of a catalyst for preparing a polyethylene having excellent copolymerizability and a high molecular weight.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a metallocene compound having a novel structure having advantages of changing the position of a substituent for increasing a molecular weight while maintaining a non-crosslinked catalyst structure, thereby being capable of implementing copolymerizability in an ansa-type catalyst level, together with a high molecular weight (Mw) of 300,000 or more, and a method of preparing the same.

Another object of the present invention is to provide a metallocene catalyst composition using the non-crosslinked metallocene compound for preparing polyethylene having high copolymerizability.

Still another object of the present invention is to provide a method of preparing polyethylene using the catalyst composition.

An exemplary embodiment of the present invention provides a metallocene compound represented by following Chemical Formula 1:

[Chemical Formula 1]

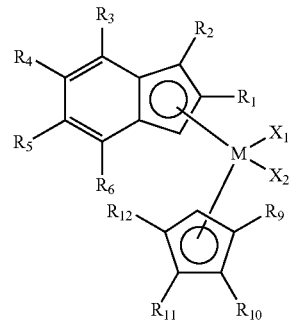

wherein $R_1$ has a structure including a 5-membered or 6-membered aromatic ring fused to a benzene ring represented by following Chemical Formula a or b,

[Chemical Formula a]

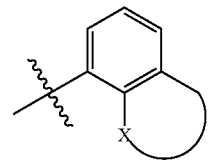

[Chemical Formula b]

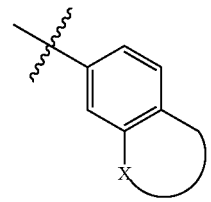

wherein X is C, N, O, or S;

$R_2$ is hydrogen;

$R_3$ to $R_6$ are identical to or different from one another, and independently of one another are hydrogen, a straight-chain or branched-chain alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

$R_9$ to $R_{12}$ are identical to or different from one another, and independently of one another are hydrogen, a straight-chain or branched-chain alkyl group having 4 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

M is a group 4 transition metal; and $X_1$ and $X_2$ are identical to or different from each other, and independently of each other are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

Another embodiment of the present invention provides a method of preparing a metallocene compound represented by Chemical Formula 1, including reacting a compound represented by following Chemical Formula 2 and a compound represented by following Chemical Formula 3:

[Chemical Formula 1]

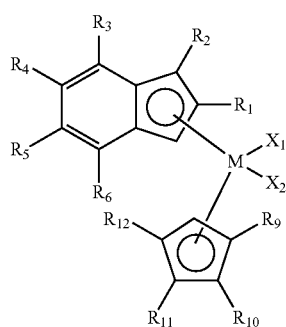

wherein $R_1$ has a structure including a 5-membered or 6-membered aromatic ring fused to a benzene ring represented by following Chemical Formula a or b,

[Chemical Formula a]

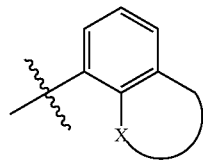

[Chemical Formula b]

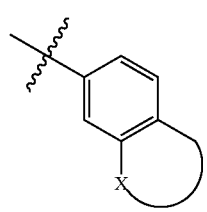

wherein X is C, N, O, or S;

$R_2$ is hydrogen;

$R_3$ to $R_6$ are identical to or different from one another, and independently of one another are hydrogen, a straight-chain or branched-chain alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

$R_9$ to $R_{12}$ are identical to or different from one another, and independently of one another are hydrogen, a straight-chain or branched-chain alkyl group having 4 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

M is a group 4 transition metal; and $X_1$ and $X_2$ are identical to or different from each other, and independently of each other are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms;

[Chemical Formula 2]

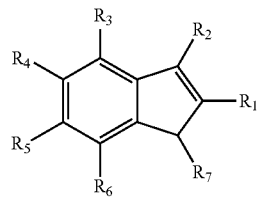

wherein $R_1$ is as defined in Chemical Formula 1; and $R_2$ to $R_7$ are identical to or different from one another, and independently of one another are hydrogen, a straight-chained or branched-chained alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

[Chemical Formula 3]

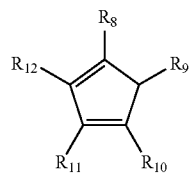

wherein $R_8$ to $R_{12}$ are identical to or different from one another, and independently of one another are hydrogen, a straight-chain or branched-chain alkyl group having 4 to 20 carbon atoms, $-MX_1X_2$, an alkenyl group having 1 to 20 carbon atoms, an aryl having 6 to 20 carbon atoms, an alkylaryl having 6 to 20 carbon atoms, or an arylalkyl having 6 to 20 carbon atoms, in which at least one of $R_8$ to $R_{12}$ is substituted by $-MX_1X_2$;

M is a group 4 transition metal; and $X_1$ and $X_2$ are identical to or different from each other, and independently of each other are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

Yet another embodiment of the present invention provides a method of preparing an olefin-based polymer including polymerizing an olefin-based monomer, in the presence of a catalyst composition including the above-described metallocene compound.

The metallocene compound according to the present invention which is a non-crosslinked catalyst provides a novel structure having a copolymerizability in an ansa-type level. Particularly, the metallocene catalyst compound of the present invention represents high copolymerizability and activity as compared with a non-crosslinked catalyst having a similar structure, and provides an effect of implementing a high molecular weight of 300,000 or more by polymerization after preparing a supported catalyst. Therefore, the polyolefin prepared by the method of the present invention may represent a broad molecular weight distribution and a high molecular weight.

DETAILED DESCRIPTION OF THE EMBODIMENTS

The terms used in the present specification are used only in order to describe exemplary embodiments rather than limiting the present invention. Singular forms are intended to include plural forms unless otherwise explicitly stated contextually. It will be further understood that the terms "comprises" or "have" used in this specification specify the presence of stated features, numerals, steps, constituent elements, or a combination thereof, but do not preclude the presence or addition of one or more other features, numerals, steps, constituent elements, or a combination thereof.

Further, the present invention may be variously modified and have several forms. Therefore, specific exemplary embodiments of the present invention will be illustrated and be described in detail below. However, it is to be understood that the present invention is not limited to a specific disclosed form, but includes all modifications, equivalents, and substitutions without departing from the scope and spirit of the present invention.

Hereinafter, the present invention will be described in detail.

According to an exemplary embodiment of the present invention, a metallocene compound represented by the following Chemical Formula 1 is provided.

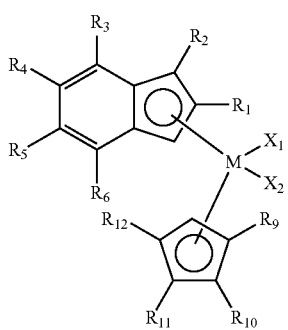

[Chemical Formula 1]

wherein $R_1$ has a structure including a 5-memberd or 6-membered aromatic ring fused to a benzene ring represented by following Chemical Formula a or b.

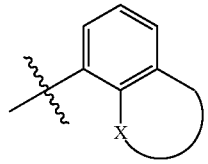

[Chemical Formula a]

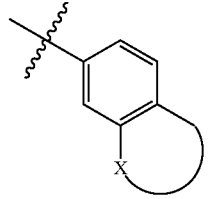

[Chemical Formula b]

wherein X is C, N, O, or S;

$R_2$ is hydrogen;

$R_3$ to $R_6$ are identical to or different from one another, and independently of one another, are hydrogen, a straight-chain or branched-chain alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

$R_9$ to $R_{12}$ are identical to or different from one another, and independently of one another, are hydrogen, a straight-chain or branched-chain alkyl group having 4 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

M is a group 4 transition metal; and $X_1$ and $X_2$ are identical to or different from each other, and independently of each other, are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

An ansa-metallocene compound is a catalyst compound including two ligands connected to each other by a bridge group, in which, by the bridge group, rotation of the ligand is prevented, and the activity and structure of a metal center are determined.

Conceiving such structural feature, it has been confirmed in the present invention that a metallocene compound having a structure including indenyl group and cyclopentadienyl group ligands to which a 5-membered or 6-membered cyclic structure is introduced is provided, thereby representing excellent catalytic features as compared with a conventional catalyst.

That is, the compound of the Chemical Formula 1 is a non-crosslinked type which is a feature of a metallocene catalyst, thereby representing high activity, and also represents copolymerizability in an ansa-type catalyst level, thereby having an effect of excellent copolymerizability with a comonomer such as 1-hexene. Further, the ligands of the indenyl group and cyclopentadienyl group may be used in the preparation of an olefin requiring high tacticity.

Therefore, the present invention may provide a method of synthesizing a transition metal catalyst having a novel structure capable of implementing high copolymerizability in a non-crosslinked ansa-type catalyst level, as compared with the conventional metallocene catalyst generally used as a polymerization catalyst in olefin polymerization.

Further, the metallocene compound of the present invention may change a substituent position for increasing a molecular weight, while maintaining a non-crosslinked catalyst structure, thereby providing an olefin-based polymer, preferably polyethylene, having a high molecular weight of 300,000 or more.

Further, the metallocene compound of the present invention may represent excellent activity without containing a general carrier, and may easily control a microstructure of an olefin-based polymer in the preparation of a polyolefin. That is, the present invention may represent an excellent effect only with the characteristic of the precursor itself without a carrier. Therefore, the metallocene compound of the present invention may be an unsupported and heterogeneous catalyst.

According to the exemplary embodiment of the present invention, in the metallocene compound of the Chemical Formula 1, substituents having a hydrocarbon adjacent to a substituent X may be linked to each other in the Chemical Formulae a and b, to form a 5-membered or 6-membered aromatic ring, and accordingly, form a structure having a ring fused to a benzene ring. Therefore, the Chemical Formulae a and b may include an indene or naphthalene structure. Further, the 5-membered or 6-membered cyclic structure in the Chemical Formulae a and b may contain nitrogen unsubstituted or substituted with an alkyl group having 1 to 20 carbon atoms. Preferably, X in the Chemical Formulae a and b is a carbon atom (C), respectively, and it is preferred to include a naphthalene structure having a 6-membered aromatic ring fused to a benzene ring.

Further, $R_2$ to $R_6$ in the Chemical Formula 1 may independently of one another be hydrogen, and $R_9$ to $R_{12}$ may independently of one another be hydrogen or a straight-chained or branched-chained alkyl group having 4 to 10 carbon atoms. More preferably, $R_2$ to $R_6$ in the Chemical Formula 1 may independently of one another be hydrogen, at least one of $R_9$ to $R_{12}$ may be a butyl group, and other substituents thereof may be hydrogen. However, the present invention is not limited thereto.

Further, M may be titanium (Ti), zirconium (Zr), or hafnium (Hf), and $X_1$ and $X_2$ may independently of each other be a halogen or an alkyl group having 1 to 20 carbon atoms, but the present invention is not limited thereto.

Further, the metallocene compound of the present invention may have catalytic activity of 7 to 15 g/mol·h.

The example of the metallocene compound represented by the Chemical Formula 1 may be any one selected from the group consisting of the compounds of the following structural formulae, but the present invention is not limited thereto.

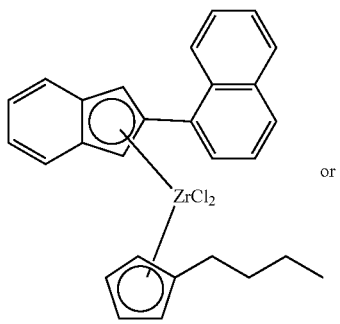

or

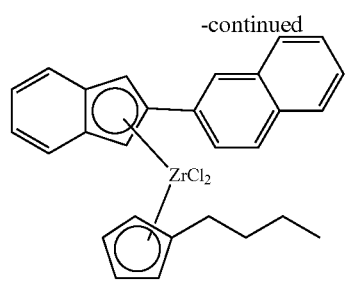

According to another aspect of the present invention, a method of preparing the metallocene compound represented by the following Chemical Formula 1, including reacting the compound represented by the following Chemical Formula 2 and the compound represented by the following Chemical Formula 3, is provided.

[Chemical Formula 1]

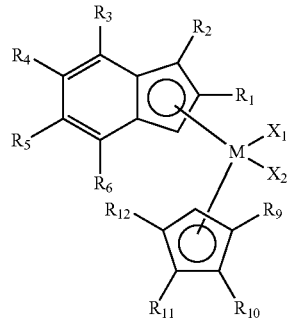

wherein $R_1$ has a structure including a 5-membered or 6-membered aromatic ring fused to a benzene ring represented by following Chemical Formula a or b.

[Chemical Formula a]

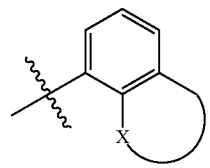

[Chemical Formula b]

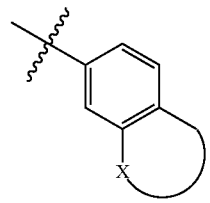

wherein X is C, N, O, or S;

$R_2$ is hydrogen;

$R_3$ to $R_6$ are identical to or different from one another, and independently of one another are hydrogen, a straight-chain or branched-chain alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

$R_9$ to $R_{12}$ are identical to or different from one another, and independently of one another are hydrogen, a straight-chain or branched-chain alkyl group having 4 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

M is a group 4 transition metal; and $X_1$ and $X_2$ are identical to or different from each other, and independently of each other are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

[Chemical Formula 2]

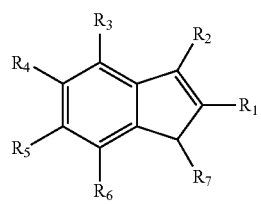

wherein $R_1$ is as defined in the Chemical Formula 1, $R_2$ and $R_7$ are independently of each other hydrogen, and $R_3$ to $R_6$ are identical to or different from one another, and independently of one another are hydrogen, a straight-chain or branched-chain alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms.

[Chemical Formula 3]

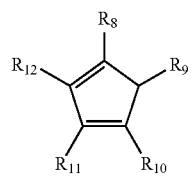

wherein $R_8$ to $R_{12}$ are identical to or different from one another, and independently of one another are hydrogen, a straight-chained or branched-chained alkyl group having 4 to 20 carbon atoms, -$MX_1X_2$, an alkenyl group having 1 to 20 carbon atoms, an aryl having 6 to 20 carbon atoms, an alkylaryl having 6 to 20 carbon atoms, or an arylalkyl having 6 to 20 carbon atoms, in which at least one of $R_8$ to $R_{12}$ is substituted with -$MX_1X_2$;

M is a group 4 transition metal; and $X_1$ and $X_2$ are identical to or different from each other, and independently of each other are a halogen an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

When the compound represented by the Chemical Formula 2 of the present invention and the compound represented by the Chemical Formula 3 of the present invention are reacted, the reaction may be carried out at a low temperature and under a solvent. Preferably, the reaction may be carried out while stirring at a temperature of −80° C. to −20° C., under an organic solvent, in the presence of a base. In the present invention, as the reaction proceeds at a low temperature, selectivity of the reaction may be raised.

The base may include n-BuLi and the like, but the present invention is not limited thereto. The compound of the Chemical Formula 2 and the compound of the Chemical formula 3 may be reacted in a mole ratio of 1:1.

Meanwhile, the compound represented by the Chemical Formula 2 may be prepared by reacting the indene-based compound of the following Chemical Formula 4 and the cyclic compound including a 5-membered or 6-membered aromatic ring of the following Chemical Formula 5 in the presence of a catalyst, under an organic solvent.

[Chemical Formula 4]

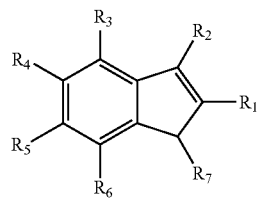

wherein $R_2$ to $R_7$ are identical to or different from one another, and independently of one another are hydrogen, a straight-chained or branched-chained alkyl group having 1 to 20 carbon atoms, an alkenyl group having 1 to 20 carbon atoms, an aryl having 6 o 20 carbon atom, an alkylaryl having 6 to 20 carbon atoms, or an arylalkyl having 6 to 20 carbon atoms; and $X_3$ is a halogen.

[Chemical Formula 5]

wherein

X is C, N, O, or S; and

A is —$B(OH)_2$ or a Grignard reagent.

In the Chemical Formula 4, $X_3$ may be a bromine atom, and $R_2$ to $R_7$ are hydrogen, respectively, but the present invention is not limited thereto. This halogen-substituted compound of the Chemical Formula 4 may be prepared by the reaction using NBS from an indene-based compound, p-toluene sulfonic acid, and the like, and the method may be carried out by a well-known reaction in an organic synthesis field.

The cyclic compound of the Chemical Formula 5 refers to inclusion of a 5-membered or 6-membered aromatic ring fused to a benzene ring.

The Grignard reagent in A of the Chemical Formula 5 may include "—MgCl or —MgBr".

Further, the compound of the Chemical Formula 5 is used as a Lewis acid, and may be used in a mole ratio of 1:1 to 2 relative to 1 mol of the compound of the Chemical Formula 4.

Further, the reaction to prepare the compound of the Chemical Formula 2 may be carried out in the presence of a palladium or a nickel-based metal catalyst. For example, when A of the Chemical formula 5 is "—B(OH)$_2$", the reaction may be carried out in the presence of a palladium catalyst. Further, when A of the Chemical Formula 5 is a Grignard reagent, the compound of the Chemical formula 2 may be obtained by a coupling reaction using a nickel-based catalyst instead of palladium.

Further, the solvent used in the preparation of the metallocene compound in the present invention may be an aromatic solvent such as toluene, benzene, and the like, THF, DMSO, and the like, used alone or in combination.

In the method of preparing the metallocene compound, a stirring process and the time therefor of each reaction are not particularly limited. Further, the purification process used for obtaining the metallocene compound may be a general process used in an organic synthesis method.

Meanwhile, according to another exemplary embodiment of the present invention, a method of preparing an olefin-based polymer, including polymerizing an olefin-based monomer in the presence of a catalyst composition including the above-described metallocene compound, is provided.

The metallocene compound represented by the Chemical Formula 1 may be used in the preparation of the polyolefin polymer, alone or in combination with a cocatalyst as a catalyst composition, and particularly a high molecular weight polyolefin may be produced with high activity. For example, when a catalyst composition including the metallocene compound represented by the Chemical formula 1 is contacted with an olefin-based monomer to carry out a polymerization process, polymerizability with a comonomer is greatly improved, thereby preparing an olefin-based polymer having a high molecular weight.

The olefin-based monomer may be one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-itocene.

Therefore, the olefin-based polymer of the present invention may include an ethylene/α-olefin copolymer polymerized from ethylene and an α-olefin-based comonomer.

As the α-olefin-based comonomer, an α-olefin having 4 or more carbon atoms may be used. For example, as the α-olefin having 4 or more carbon atoms, 1-butene, 1-pentene, 1-hexene, 4-methyl-1-pentene, 1-octene, 1-decene, 1-dodecene, 1-tetradecene, 1-hexadecene, 1-octadecene, and the like as described above may be mentioned, but is not limited thereto. Among these, an α-olefin having 4-10 carbon atoms is preferred, and one or various kinds of α-olefins may be used together as a comonomer.

Further, the polymerization reaction in the present invention may be carried out by homopolymerizing 1 olefin monomer, or copolymerizing 2 or more monomers, using one continuous slurry polymerization reactor, a loop slurry reactor, a gaseous reactor, or a solution reactor.

Polymerization of the olefin-based monomer may proceed by performing reaction at a temperature of about 25 to about 500° C. and about 1 to about 100 kgf/cm$^2$ for about 1 to about 24 h. Specifically, polymerization of the olefin-based monomer may be carried out at a temperature of about 25 to about 500° C., preferably about 25 to about 200° C., more preferably about 50 to about 100° C. Further, reaction pressure may be about 1 to about 100 kgf/cm$^2$, preferably about 1 to about 50 kgf/cm$^2$, and more preferably about 5 to about 40 kgf/cm$^2$.

The present invention may further include a cocatalyst in the catalyst composition, if necessary, and the kind thereof is not particularly limited.

Preferably, the catalyst composition may further include one or more cocatalysts selected from the group consisting of the compounds represented by following Chemical Formulae 6, 7, and 8.

$$—[Al\ R_{13}—O]_n—$$ [Chemical Formula 6]

wherein each $R_{13}$ is identical to or different from each other, and independently of each other is a halogen, a hydrocarbon having 1 to 20 carbon atoms, or a hydrocarbon having 1 to 20 carbon atoms substituted with a halogen; and n is an integer of 2 or more.

$$J(R_{13})_3$$ [Chemical Formula 7]

wherein $R_{13}$ is as defined in the Chemical Formula 8; and

J is aluminum or boron.

$$[E-H]^+[ZA'_4]^-\ or\ [E]^+[ZA'_4]^-$$ [Chemical Formula 8]

wherein

E is a neutral or positive ionic Lewis acid;

H is a hydrogen atom;

Z is a group 13 element; and each A' is identical to or different from each other, and independently of each other is an aryl group having 6 to 20 carbon atoms or an alkyl group having 1 to 20 carbon atoms in which one or more hydrogen atoms is unsubstituted or substituted by a halogen, a hydrocarbon having 1 to 20 carbon atoms, an alkoxy, or a phenoxy.

Examples of the compound represented by the Chemical Formula 6 includes methylaluminoxane, ethylaluminoxane, isobutylaluminoxane, butylaluminoxane, or the like, and a more preferred compound is methylaluminoxane.

Examples of the compound represented by the Chemical Formula 7 include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, or the like, and a more preferred compound is selected from the group consisting of trimethylaluminum, triethylaluminum, and triisobutylaluminum.

Examples of the compound represented by the Chemical Formula 8 include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N, N-diethylanilinium tetraphenylboron, N, N-diethylanilinium tetrapentafluorophenylboron, diethylammoniumtetrapentafluorophenylboron, triphenylphosphonium tetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o, p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, tripropylammoniumtetra(p-tolyl)boron, triethylammoniumtetra(o,p-dimethylphenyl) boron, tributylammoniumtetra(p-trifluoromethylphenyl) boron, triphenylcarboniumtetra(p-trifluoromethylphenyl) boron, triphenylcarboniumtetrapentafluorophenylboron, or the like.

Preferably, as the cocatalyst, alumoxane, and more preferably, methylalumoxane (MAO) which is an alkyl alumoxane may be used.

Further, the mole ratio of the metallocene compound and the cocatalyst compound in the present invention is 1:10 to 10:1, is but not particularly limited thereto.

In addition, the catalyst composition may further include a reaction solvent, and the reaction solvent includes a hydrocarbon-based solvent such as pentane, hexane, or heptane, an aromatic-based solvent such as benzene or toluene, or the like, but is not limited only thereto.

An olefin-based polymer prepared in the above-described manner may have a high molecular weight, preferably a weight average molecular weight of 300,000 or more. Further, according to an exemplary embodiment of the present invention, in the case of the olefin-based polymer, the mol % (branch) of α-olefin relative to an ethylene monomer may be 4 to 8 mol %.

Hereinafter, the operation and the effect of the invention will be described in detail, through the specific examples of the invention. However, the examples are only presented to illustrate the invention, whereby the scope of the invention is not defined.

EXAMPLES

The organic reagent and solvent used in the following examples were purchased from Aldrich, and were purified by a standard method unless otherwise stated. Contact between air and moisture was blocked to increase reproducibility of the experiments in all steps in the synthesis.

Example 1

(1) Synthesis of Bromohydrin

To a 500 mL flask, 35 mL (300 mmol) of indene was added, and diluted in 150 mL of DMSO and 15 mL of water. This solution was cooled to 0° C., and then 53 g of N-bromosuccinimide (300 mmol, 1 equiv.) was slowly added to the solution over 10 min. After 2 h, the reactant was poured into 800 mL of water, and the resulting crystal was washed with a sufficient amount of water while being filtered, thereby obtaining bromohydrin in the form of a while crystal in a yield of about 80%.

$^1$H NMR (500 MHz, CDCl$_3$): δ 3.24 (1H, m), 3.60 (1H, m), 4.30 (1H, m), 5.33 (1H, m), 7.23-7.32 (3H, m), 7.44 (1H, m)

(2) Synthesis of 2-bromoindene 25 g was taken from the bromohydrin compound obtained from the above reaction, dissolved in 300 mL of toluene, then 500 mg of p-toluene sulfonic acid was added thereto, and the temperature was raised to 90° C., and stirring was carried out for 20 h. After the reactant was cooled to room temperature, it was washed with a sufficient amount of water, dehydrated with MgSO$_4$, and filtered and dried under reduced pressure, thereby obtaining a brown concentrate. This was dissolved in about 100 mL of hexane, and hexane was filtered as an eluent through a silica pad, thereby obtaining non-viscous yellow oil (2-bromoindene) in a yield of 60 to 70%.

$^1$H NMR (500 MHz, CDCl$_3$): δ 3.61 (3H, s), 6.95 (1H, s), 7.18-7.20 (3H, m), 7.27-7.32 (1H, m), 7.39 (1H, m)

(3) Synthesis of 1-(1H-indene-2-yl)naphthalene

Finally, 2.7 g (13.8 mmol) of 2-bromoindene was added to a 100 mL Schlenk flask, and dissolved in a mixed solution of 60 mL of DME (dimethyl ether) and 20 mL of water. 3.4 g (18 mmol) of 1-naphthalene boronic acid and 2.8 g (21 mmol) of K$_2$CO$_3$ were added thereto, and argon gas was bubbled therein for 10 min to remove oxygen in the solvent. Thereafter, heating was initiated under an argon gas atmosphere, and when the temperature reached 90° C., 800 mg (0.7 mmol, 5 mol %) of palladium(0)tetrakis(triphenylphosphine) (Pd/C) was added thereto, and stirred for 6 h. Thereafter, the reaction mixture was cooled to room temperature, and 200 mL of water was poured therein to filter resulting brown precipitates, which were washed with about 50 mL of ether and then dried, thereby obtaining 2.4 g (67%) of a white solid.

$^1$H NMR (500 MHz, CDCl$_3$): δ 3.95 (2H, s), 7.20-7.39 (7H, s), 7.82-7.87 (4H, m), 8.00 (1H, s)

(4) Synthesis of Compound (A-1) of the Chemical Formula 1 Represented by the Following Structural Formula

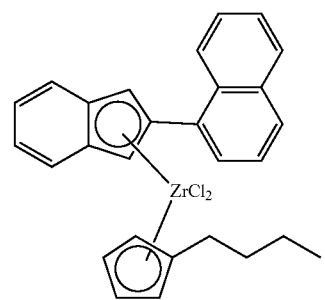

1.50 g (6.2 mmol) of 1-(1H-indene-2-yl)naphthalene was added to a 250 mL Schlenk flask, and dissolved in 40 mL of toluene and 20 mL of THF. This solution was cooled to 0° C., and then 3 mL (7.5 mmol) of a 2.5 M nBuLi solution was added. This reaction mixture was stirred at room temperature for a day, and then 11.6 g (6.2 mmol) of a stock solution of (2-butylcyclopenta-2,4-dienyl)zirconium(IV) chloride was slowly added thereto at −78° C. The reactant was stirred at room temperature for a day, then distilled under reduced pressure until the volume of the solvent was ¹/₁₀ of the initial volume, and then 100 mL of hexane was added thereto. The precipitates produced herein were separated through filtration to obtain 2.2 g of a yellow powder.

$^1$H NMR (500 MHz, CDCl$_3$): δ 0.80 (3H, t), 1.23 (2H, m), 1.35 (2H, m), 2.42 (2H, t), 5.80 (1.5H, t), 5.93 (1.5H, t), 7.05 (2H, m), 7.29 (2H, m), 7.49 (2H, m), 7.66 (2H, m), 7.85 (2H, m), 8.17 (1H, s)

Example 2

(1) Synthesis of Bromohydrin 35 mL (300 mmol) of indene was added to a 500 mL flask, and dissolved in 150 mL DMSO and 15 mL of water. After this solution was cooled to 0° C., 53 g (300 mmol, 1 equiv.) of N-bromosuccinimide was slowly added over 10 min. After 2 h, the reactant was poured into 800 mL of cold water, and the resulting crystal was washed with a sufficient amount of water while being filtered, thereby obtaining bromohydrin in the form of a while crystal in a yield of about 80%.

$^1$H NMR (500 MHz, CDCl$_3$): δ 3.24 (1H, m), 3.60 (1H, m), 4.30 (1H, m), 5.33 (1H, m), 7.23-7.32 (3H, m), 7.44 (1H, m)

(2) Synthesis of 2-bromoindene 25 g was taken from the bromohydrin compound obtained from the above reaction, and dissolved in 300 mL of toluene, then 500 mg of p-toluene sulfonic acid was added thereto, the temperature was raised to 90° C., and stirring was carried out for 20 h or more. After the reactant was cooled to room temperature, it was washed with a sufficient amount of water, dehydrated with MgSO$_4$, and filtered and dried under reduced pressure, thereby obtaining a brown concentrate. This was dissolved in about 100 mL of hexane, and hexane was filtered as an eluent through a silica pad, thereby obtaining a non-viscous yellow oil (2-bromoindene) in a yield of 60 to 70%.

$^1$H NMR (500 MHz, CDCl$_3$): δ 3.61 (3H, s), 6.95 (1H, s), 7.18-7.20 (3H, m), 7.27-7.32 (1H, m), 7.39 (1H, m)

(3) Synthesis of 2-(1H-indene-2-yl)naphthalene

Finally, 2.7 g (13.8 mmol) of 2-bromoindene was added to a 100 mL Schlenk flask, and dissolved in a mixed solution of 60 mL of DME (dimethyl ether) and 20 mL of water. 3.4 g (18 mmol) of 2-naphthalene boronic acid and 2.8 g (21 mmol) of K$_2$CO$_3$ were added thereto, and argon gas was bubbled therein for 10 min to remove oxygen in the solvent. Thereafter, heating was initiated under an argon atmosphere, and when the temperature reached 90° C., 800 mg (0.7 mmol, 5 mol %) of palladium(0)tetrakis(triphenylphosphine) (Pd/C) was added thereto, and stirred for 6 h. Thereafter, the reaction mixture was cooled to room temperature, and 200 mL of water was poured thereto to filter the resulting brown precipitate, which was washed with about 50 mL of ether, and then dried, thereby obtaining 2.4 g (67%) of a white solid.

$^1$H NMR (500 MHz, CDCl$_3$): δ 3.96 (2H, s), 7.23 (1H, m), 7.31 (1H, m), 7.48-7.54 (4H, m), 7.69-7.74 (1H, m), 7.76-7.83 (4H, m), 8.01 (1H, s).

(4) Synthesis of Compound (A-2) of the Chemical Formula 1 represented by following structural formula

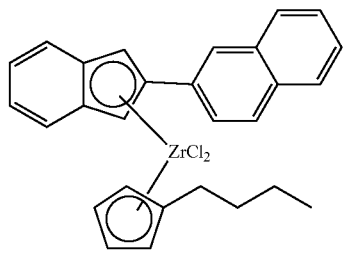

1.50 g (6.2 mmol) of 2-(1H-indene-2-yl)naphthalene was added to a 250 mL Schlenk flask, and dissolved in 40 mL of toluene and 20 mL of THF. This solution was cooled to 0° C., and 3 mL (7.5 mmol) of a 2.5 M nBuLi solution was added thereto. This reaction mixture was stirred at room temperature for a day, and thereafter, 11.6 g (6.2 mmol) of a stock solution of (3-butylcyclopenta-2,4-dienyl)zirconium (IV) chloride was slowly added at −78° C. The reactant was stirred at room temperature for a day, then distilled under reduced pressure until the volume of the solvent was 1/10 of the initial volume, and then 100 mL of hexane was added thereto. The precipitate produced herein was separated through filtration to obtain 2.2 g of a yellow powder.

$^1$H NMR (500 MHz, CDCl$_3$): δ 0.78-0.82 (3H, m), 1.17-1.19 (2H, m), 1.33-1.36 (2H, m), 2.40-2.44 (2H, m), 5.80 (1.5H, s), 5.92 (1.5H, s), 7.04 (1H, m), 7.29 (2H, m), 7.53 (2H, m), 7.62 (2H, m), 7.87-7.93 (4H, m), 8.17 (1H, s).

Comparative Example 1

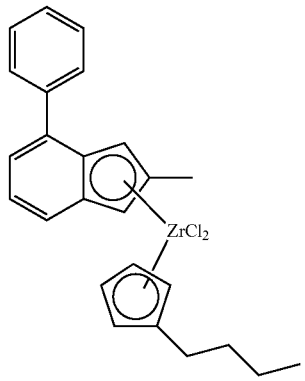

3.1 g (15.0 mmol) of 2-methyl-7-phenyl-1H-indene was added to a 250 mL Schlenk flask, and dissolved in 40 mL of toluene and 20 mL of THF. This solution was cooled to 0° C., and then 6 mL (15 mmol) of a 2.5 M nBuLi solution was added thereto. This reaction mixture was stirred at room temperature for a day, and thereafter, 37 g (15 mmol) of a stock solution of (3-butylcyclopenta-2,4-dienyl)zirconium (IV) chloride was slowly added thereto at −78° C. The reactant was stirred at room temperature for a day, then distilled under reduced pressure until the volume of the solvent was 1/10 of the initial volume, and then 100 mL of hexane was added thereto. The precipitate produced herein was separated through filtration to obtain 2.2 g of a yellow powder.

$^1$H NMR (500 MHz, CDCl$_3$): δ 0.85 (3H, m), 1.23 (2H, m), 1.37 (2H, m), 2.44 (3H, s), 2.49 (2H, m), 5.59 (0.5H, s), 5.72 (0.5H, s), 5.78 (0.5H, s), 5.89 (0.5H, s), 6.54 (1H, d), 7.11 (1H, m), 7.26-7.29 (2H, m), 7.42-7.52 (4H, m), 7.74 (1H, m).

Comparative Example 2

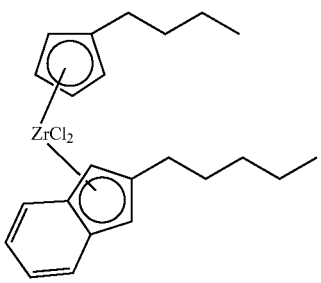

1.86 g (10.0 mmol) of 2-pentyl-1H-indene was added to a 250 mL Schlenk flask, and dissolved in 50 mL of THF. This solution was cooled to 0° C., and then 4.4 mL (11 mmol) of a 2.5 M nBuLi solution was added. This reaction mixture was stirred at room temperature for a day, and then 24 g (10 mmol) of a stock solution of (3-butylcyclopenta-2,4-dienyl)zirconium(IV) chloride was slowly added thereto at −78° C. The reactant was stirred at room temperature for a day, then distilled under reduced pressure until the volume of the solvent was 1/10 of the initial volume, and then 100 mL of hexane was added thereto. The precipitate produced herein was separated through filtration to obtain 1.8 g of a yellow powder.

$^1$H NMR (500 MHz, CDCl$_3$): δ 0.87 (6H, s), 1.24-1.36 (6H, m), 1.41 (2H, m), 1.54 (2H, m), 2.49 (2H, m), 2.66 (2H, m), 2.77 (2H, m), 5.62 (1H, s), 5.85 (1H, s), 6.34 (1H, s), 6.43 (1H, s), 6.72 (2H, s), 7.22 (2H, m), 7.65 (2H, m).

Example 3 and Comparative Examples 3 and 4

Preparation of Copolymer

A catalyst (20 μmol) was placed in a flask under an argon atmosphere, to which 20 mL of toluene was added and stirred, thereby forming a 1 mM catalyst solution. Herein, as the catalyst, the catalysts of above Examples 1 and 2 and Comparative Examples 1 and 2 were used, respectively.

Thereafter, two 100 mL Andrew bottles were prepared and assembled with an impeller part, and then the inside was replaced with argon in a glove box. After the globe box treatment, to the inside of the each Andrew bottle treated with a small amount of TMA, 70 mL of toluene was added, and 10 mL of a MAO solution (10 wt % toluene) was injected. 5 mL of a 1 mM catalyst solution (toluene) (5 μmol) was injected into the reactor. With each one soaked in an oil bath heated to 90° C., a mechanical stirrer was fixed to an upper portion of the bottle, and thereafter, to one of the two Andrew bottles, 5 mL of 1-hexane to be used as a comonomer was injected. After the inside of the bottle was purged with ethylene gas three times, an ethylene valve was opened, and a mechanical stirrer was operated to perform the reaction at 500 rpm for 30 min. During the reaction, a vortex line in the inside of the vessel was often checked, and when the line was flat, the reaction was quickly finished. After the reaction, the temperature was lowered to room temperature, and then gas in the inside of the vessel was vented. Then, the content was poured into about 400 mL of ethanol, stirred for about 1 h, and subjected to filtration to obtain a polymer which was dried for 20 h in a vacuum oven set at 60° C.

The mass of the obtained polymer was calculated, from which the activity of the catalyst was calculated, and 10 mg of a sample was taken therefrom to perform GPC analysis, thereby confirming a molecular weight and a distribution degree. The results are listed in following Table 1.

TABLE 1

| | Catalyst | 1-hexene (mL) | Activity [a] × 10$^6$ | Mw [b] (g/mol) | PDI [b] | Branch (1-hexene mol %) |
|---|---|---|---|---|---|---|
| Example 1 | A-1 | — | 10.0 | 79,700 | 9.5 | — |
| | A-1 | 5.0 | 13.7 | 38,700 | 10.3 | 5.3 |
| Example 2 | A-2 | — | 7.9 | 53,300 | 7.1 | |
| | A-2 | 5.0 | 8.3 | 39,400 | 7.8 | 4.3 |
| Comparative Example 1 | | — | 5.7 | 87,500 | 5.0 | |
| | | 5.0 | 5.2 | 30,400 | 7.1 | 3.1 |
| Comparative Example 2 | | — | 2.1 | 71,000 | 5.3 | |
| | | 5.0 | 3.6 | 44,500 | 5.6 | 3.3 |

Conditions: catalytic amount (5 μmol), ethylene pressure (PE = 50 psig), Al/Zr = 3000, Temperature: 90° C., reaction time: 30 min.
[a] g/mol · h
[b] GPC In view of the Table 1, the metallocene compounds of Examples 1 and 2 of the present invention have high catalytic activity and excellent comonomer reactivity, as compared with the general metallocene compounds of Comparative Examples 1 and 2, thereby allowing easy preparation of a polyolefin having a high molecular weight.

Particularly, in the case of using the catalyst of Comparative Example 2 to which a cyclic structure is not introduced, and having a straight-chained alkyl group, the catalytic activity is very low, so that it was difficult to effectively prepare a polyolefin having a high molecular weight.

Therefore, it was recognized that Comparative Examples 1 and 2 caused a problem of reducing productivity when preparing a polyolefin having a high molecular weight.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A metallocene compound represented by following Chemical Formula 1:

[Chemical Formula 1]

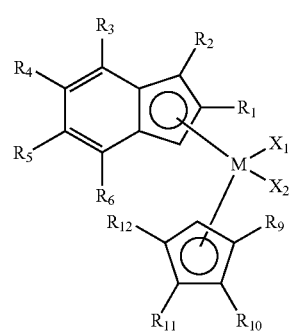

wherein

R₁ has a structure including a 5-membered or 6-membered aromatic ring fused to a benzene ring represented by following Chemical Formula a or b:

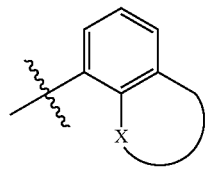

[Chemical Formula a]

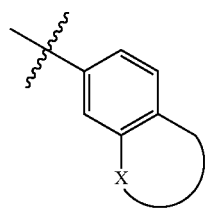

[Chemical Formula b]

wherein X is C, N, O, or S;

R₂ to R₆ are identical to or different from one another, and independently of one another are hydrogen, a straight-chained or branched-chained alkyl group having 1 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

R₉ to R₁₂ are identical to or different from one another, and independently of one another are hydrogen, a straight-chained or branched-chained alkyl group having 4 to 20 carbon atoms, an alkenyl group having 1 to 20 carbon atoms, an aryl having 6 to 20 carbon atoms, an alkylaryl having 6 to 20 carbon atoms, or an arylalkyl having 6 to 20 carbon atoms;

M is a group 4 transition metal; and

X₁ and X₂ are identical to or different from each other, and independently of each other are a halogen, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

2. The metallocene compound of claim 1, wherein X in the Chemical formulae a and b is a carbon atom (C), respectively, and includes a naphthalene structure having a 6-membered aromatic ring fused to a benzene ring.

3. The metallocene compound of claim 1, wherein in the Chemical Formula 1, R₂ to R₆ are independently of one another hydrogen, and R₉ to R₁₂ are independently of one another hydrogen, or a straight-chained or branched-chained alkyl group having 4 to 10 carbon atoms.

4. The metallocene compound of claim 1, wherein M is titanium (Ti), zirconium (Zr), or hafnium (Hf).

5. The metallocene compound of claim 1, wherein X₁ and X₂ are independently of each other a halogen or an alkyl group having 1 to 20 carbon atoms.

6. The metallocene compound of claim 1, wherein the compound represented by the Chemical Formula 1 is any one selected from the group consisting of the compounds of following structural formulae:

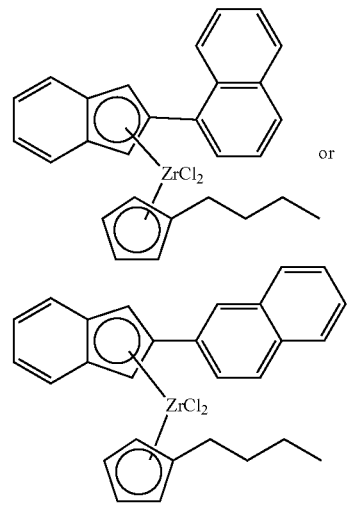

or

7. A method of preparing an olefin-based polymer, comprising
polymerizing an olefin-based monomer
in the presence of a catalyst composition including the metallocene compound of claim 1.

8. The method of claim 7, wherein the olefin-based monomer is one or more selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-itocene.

9. The method of claim 7, wherein the catalyst composition further includes one or more cocatalysts selected from the group consisting of compounds represented by following Chemical Formulae 6, 7, and 8:

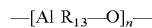  [Chemical Formula 6]

wherein each R₁₃ is identical to or different from each other, and independently of each other are a halogen, a hydrocarbon having 1 to 20 carbon atoms, or a hydrocarbon having 1 to 20 carbon atoms substituted with a halogen; and n is an integer of 2 or more;

  [Chemical Formula 7]

wherein

R₁₃ is as defined in the Chemical Formula 6; and
J is aluminum or boron;

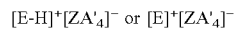  [Chemical Formula 8]

wherein

E is a neutral or positive ionic Lewis acid;
H is a hydrogen atom;
Z is a group 13 element;
each A' is identical to or different from each other, and independently of each other are an aryl group having 6 to 20 carbon atoms or an alkyl group having 1 to 20 carbon atoms in which one or more hydrogen atoms are unsubstituted or substituted by a halogen, a hydrocarbon having 1 to 20 carbon atoms, an alkoxy, or a phenoxy.

* * * * *